US008045266B2

(12) United States Patent
Nakamura

(10) Patent No.: US 8,045,266 B2
(45) Date of Patent: Oct. 25, 2011

(54) BINOCULAR LOUPE

(75) Inventor: Shoichi Nakamura, Higashichikuma-gun (JP)

(73) Assignees: Shoichi Nakamura, Nagano (JP); ACP Japan, Co., Ltd., Tokyo (JP)

( * ) Notice: Subject to any disclaimer, the term of this patent is extended or adjusted under 35 U.S.C. 154(b) by 823 days.

(21) Appl. No.: 12/083,595

(22) PCT Filed: Jan. 27, 2006

(86) PCT No.: PCT/JP2006/301314
§ 371 (c)(1),
(2), (4) Date: Apr. 15, 2008

(87) PCT Pub. No.: WO2007/057987
PCT Pub. Date: May 24, 2007

(65) Prior Publication Data
US 2009/0231699 A1    Sep. 17, 2009

(30) Foreign Application Priority Data

Nov. 16, 2005    (JP) .............................. 2005-009620 U

(51) Int. Cl.
*G02B 25/00*    (2006.01)
(52) U.S. Cl. .................... 359/481; 359/410; 359/480

(58) Field of Classification Search .................. 359/410, 359/425, 480–482
See application file for complete search history.

(56) References Cited

U.S. PATENT DOCUMENTS 2,935,910 A * 5/1960 Schmidt ........................ 359/481

FOREIGN PATENT DOCUMENTS

| JP | H05-257802 | 10/1993 |
| JP | 2004-053910 | 2/2004 |
| JP | 2004-138870 | 5/2004 |
| JP | 2004-317955 | 11/2004 |
| JP | 2005-018068 | 1/2005 |
| JP | 2005-128305 | 5/2005 |
| WO | WO2004/083941 | * 9/2004 |

* cited by examiner

*Primary Examiner* — Joshua L Pritchett
(74) *Attorney, Agent, or Firm* — Manabu Kanesaka

(57) ABSTRACT

Provided is a binocular loupe capable of adapting to current vision of a worker of a medical operation or precise operation in operating.
The binocular loupe has frame means, a pair of binocular loupe bodies, attaching means for fixing the binocular loupe bodies to the frame means, focus adjusting means for adjusting a focal length of each of the binocular loupe bodies, and supporting means for detachably attaching the focus adjusting means to eyepiece portions of the binocular loupe bodies.

4 Claims, 10 Drawing Sheets

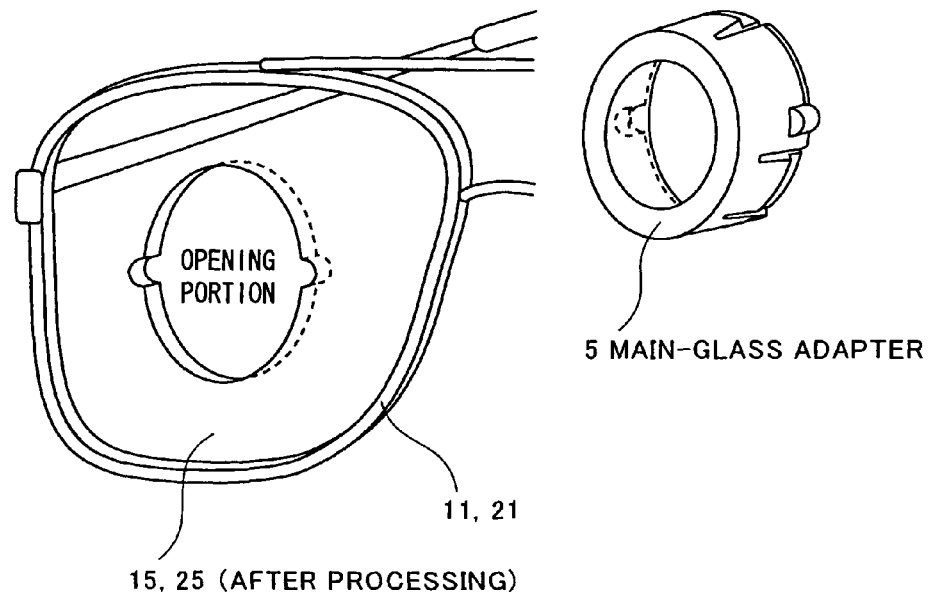
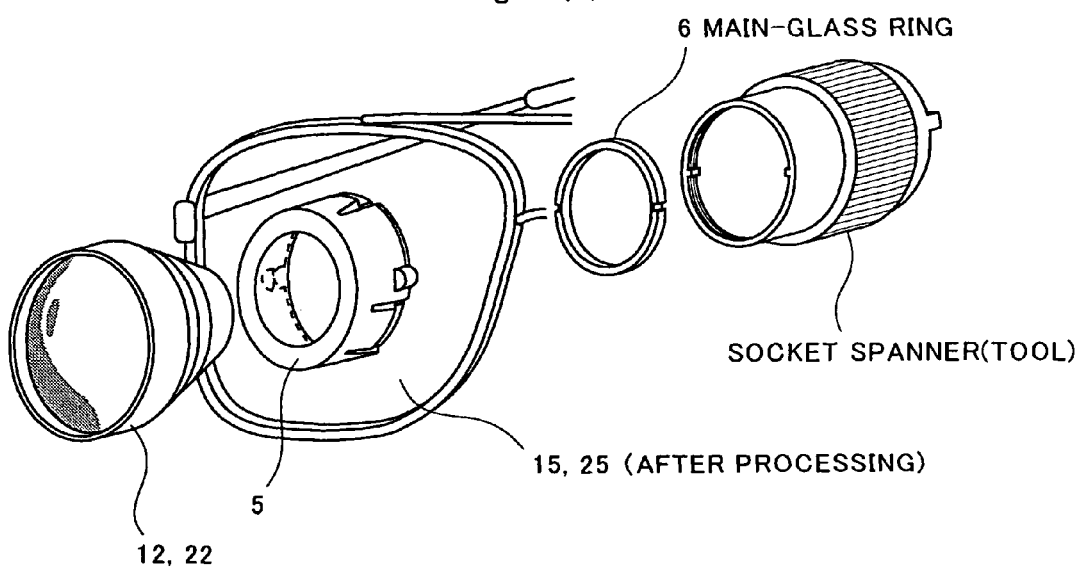

BINOCULAR LOUPE

TECHNICAL FIELD

The present invention relates to a binocular loupe used in medical operations and precision work operation, and more particularly, to an embedded type of binocular loupe where the binocular loupe is attached to glass portions of an eyeglass frame.

BACKGROUND ART

Binocular loupes have conventionally been used widely in each field such as the medical field, precision work, jewel processing and the like, as means for magnifying a local visual subject at hand to visually identify. In these fields, high precision is required in the work and operation, and particularly, in the medical field, since the field involves human lives, vision correction and astigmatism correction of the binocular loupe is required to precisely adapt to the vision of a worker.

Further, in addition to excellent resolution, wide viewing diameter, deep focal length and the like, since bright clear image quality is required, and ease in handling and ease in maintenance is demanded, waterproof processing enabling water washing, and anti-corrosion processing is needed. Further, it is necessary to configure adjustments of magnification of a main-glass loupe to be adjustable according to the use.

As an example of such a binocular loupe, Patent Document 1 discloses a structure of a binocular loupe enabling adjustments of a pupil distance i.e. attachment positions in the horizontal direction of eyepiece barrels.

Patent Document 1: Japanese Patent Publication No. 2005-257802

DISCLOSURE OF INVENTION

Problems to be Solved by the Invention

However, in such a conventional binocular loupe, although high precision is required in manual operation of a precise worker, since it is difficult to adapt the degree of lenses to correct the vision of the worker suitably to the vision of the worker in operating, there is a problem that fluctuations occur in visual precision caused by a variation in vision of the worker in operating. In other words, irrespective of the fact that human vision always varies corresponding to the extents of the health and fatigue and differs between the morning and the afternoon even in the same day, since the conventional binocular loupe is not devised to adapt to the varying vision of the worker, the worker should work using the binocular loupe with unsuitable vision, or a single worker needs to beforehand prepare a plurality of kinds of binocular loupes with different focal lengths.

The present invention was carried out in view of the foregoing, and it is an object of the invention to provide a binocular loupe capable of supporting as appropriate always varying vision of a person performing a medical operation such as a surgeon and the like and a worker performing precise operation and the like. Further, it is another object of the invention to provide a binocular loupe enabling its operation for vision adjustments to be performed with extremely ease.

Means for Solving the Problem

To solve the above-mentioned problems, a binocular loupe according to the invention is a binocular loupe to magnify a subject at hand to see, and provided with frame means, a pair of binocular loupe bodies, attaching means for fixing the binocular loupe bodies to the frame means, focus adjusting means for adjusting a focal length of each of the binocular loupe bodies, and supporting means for detachably attaching the focus adjusting means to eyepiece portions of the binocular loupe bodies.

Thus, the binocular loupe according to the invention enables the focus adjusting means to correct vision of the worker to be detachably attached to eyepiece portions of the binocular loupe bodies, and is capable of supporting the varying vision of the worker as appropriate.

Herein, the attaching means has a main-glass attaching frame, a main-glass attaching carrier lens which has an opening and is fixed by the main-glass attaching frame, and a main-glass attaching portion fitted into the opening of the main-glass attaching carrier lens.

Further, as the focus adjusting means, a plurality of kinds with different focal lengths is beforehand prepared, and one of the kinds is selected and attached to the supporting means.

Then, each of the focus adjusting means and each of the binocular loupe bodies is provided with either a convex portion or a concave portion to engage the adjusting means and the bodies with one another, and it is thus made ease that the focus adjusting means is attached and detached to/from the binocular loupe bodies.

Further, in the binocular loupe, positioning lines are marked on the focus adjusting means and the binocular loupe bodies to engage the adjusting means and the bodies with one another in predetermined positions, and it is thus possible to also correct astigmatism properly.

Moreover, by providing each of two joint faces that joins the focus adjusting means and each of the binocular loupe bodies with either a magnet plate or an iron plate, it is thus made extremely ease that the focus adjusting means is attached and detached to/from the binocular loupe bodies. Also in this case, by providing each of two joint faces that joins the focus adjusting means and each of the binocular loupe bodies with either a convex portion or a concave portion to engage the adjusting means and the bodies with one another in predetermined positions, suitable positioning is allowed.

Further, each of two joint faces that joins the focus adjusting means and each of the binocular loupe bodies is provided with a flange portion to enlarge the area of each of the faces, and each of the magnet plate and the iron plate is installed in the flange portion.

Advantageous Effect of the Invention

As described above, according to the binocular loupe of the invention, the detachable focus adjusting means enabling the focus of the binocular loupe bodies to be adjusted can be attached to the eyepiece portions of the binocular loupe bodies optionally, and it is thereby possible to provide the binocular loupe capable of adapting suitably to the current vision in operating a medial operation, precision processing or the like by easy attaching operation.

Further, since the focus adjusting means can be selected as appropriate from among a plurality of pieces of the focus adjusting means with different specifications, such an effect is produced that a precise worker is capable of selecting the adjusting means suitable for his/her vision in operation as appropriate. Furthermore, in attaching the focus adjusting means to the binocular loupe bodies, since it is configured to enable accurate positioning between the adjusting means and the bodies, also when the binocular loupe bodies support astigmatism, it is possible to secure the optimal vision by accurate positioning.

BRIEF DESCRIPTION OF THE DRAWINGS

FIGS. 5(c) and 5(d) illustrate a structure of a main-glass attaching carrier lens of the binocular loupe and a structure of a binocular loupe body according to the embodiments of the invention (2/2);

BEST MODE FOR CARRYING OUT THE INVENTION

Figure 1:
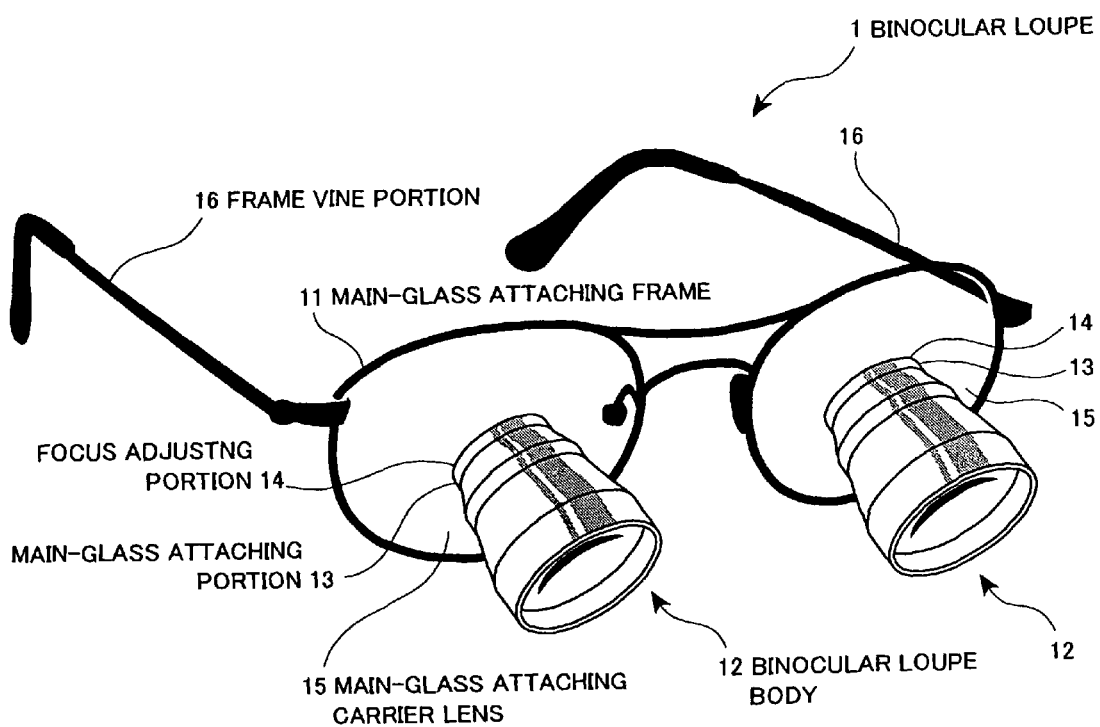
FIG. 1 shows an entire configuration of a binocular loupe according to an embodiment of the invention.

A first embodiment of the binocular loupe of the invention will specifically be described below with reference to accompanying drawings. FIG. 1 is a configuration diagram to showing an entire configuration of the binocular loupe according to this embodiment of the invention. As shown in FIG. 1, the binocular loupe 1 of this embodiment has a main-glass attaching frame 11 with the same structure as that of eyeglasses, binocular loupe bodies (main glasses) 12 to magnify an image targeted for operation, main-glass attaching portions 13 to attach the binocular loupe bodies 12 to the main-glass attaching frame 11, focus adjusting portions 14 enabling compensation for vision of a precise worker, main-glass attaching carrier lenses 15 to attach the binocular loupe bodies 12, and frame vine portions 16 to be mounted on the precise worker.

Used as a material constituting the main-glass attaching frame 18 and the frame vine portions 16 are metal such as titanium and the like with corrosion resistance and flexibility, synthetic resin and the like. Further, into the binocular loupe bodies 12 are incorporated optical systems to magnify an image targeted for operation with a group of lenses. A detail structure of the main-glass attaching portions 13 will specifically be described in FIG. 4.

Into each of the focus adjusting portions 14 is incorporated a detachable focus adjustment lens unit (see FIG. 7) to make fine adjustments of the focus of each of the binocular loupe bodies 12. The focus adjusting portions 14 can be selected from among a plurality of focus adjusting portions with different specifications to be adapted to the current vision of a precise worker. Further, a material constituting the main-glass attaching carrier glasses 15 does not need to be always transparent, but preferably transparent to expand a field of view at hand of the precise worker, and may be correction lenses when the vision needs to be corrected, or simply transparent glasses when the vision does not need to be corrected. A material of the lenses is glass or plastic. In addition, the binocular loupe 1 as shown in FIG. 1 has a magnification of 2.5 times.

Figure 2:
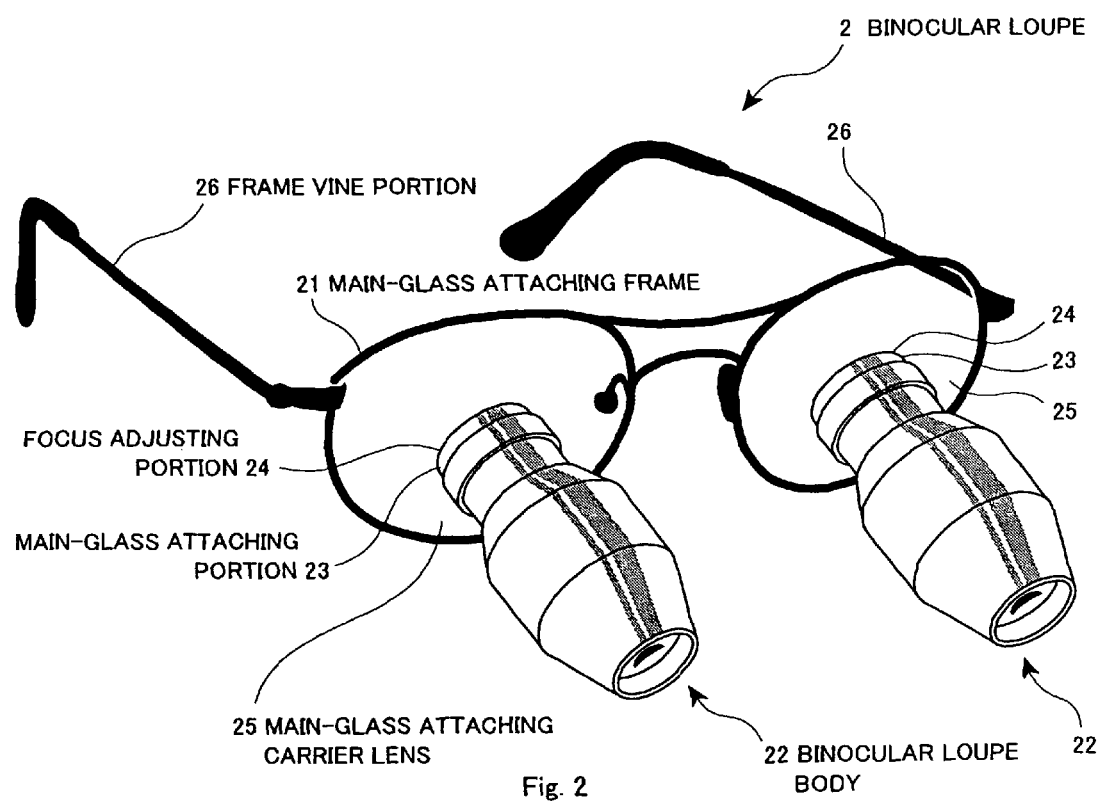
FIG. 2 shows an entire configuration of a binocular loupe according to another embodiment of the invention.

FIG. 2 is a configuration diagram showing an entire configuration of the binocular loupe according to a second embodiment of the invention. In FIG. 2, the binocular loupe 2 of this embodiment has a main-glass attaching frame 21 with the same structure as that of eyeglasses, binocular loupe bodies 22 to magnify an image targeted for operation, main-glass attaching portions 23 to attach the binocular loupe bodies 22 to the main-glass attaching frame 21, focus adjusting portions 24 enabling correction of vision of a precise worker, main-glass attaching carrier lenses 25 to attach the binocular loupe bodies 22, and frame vine portions 26 constituting the frame to be mounted on a face of the precise worker.

Used as a material constituting the main-glass attaching frame 21 are metal such as titanium and the like with corrosion resistance and flexibility, synthetic resin and the like. Further, into the binocular loupe bodies 22 are incorporated optical systems to magnify an image targeted for operation with a group of lenses. Details of the optical systems will specifically be described later in the explanation of FIG. 6. Further, into each of the focus adjusting portions 24 is incorporated a detachable focus adjustment lens unit (see FIG. 7) to make fine adjustments of the focus of each of the binocular loupe bodies 22. The focus adjusting portions 24 can be selected from among a plurality of focus adjusting portions with different specifications to be adapted to the current vision of a precise worker.

A material constituting the main-glass attaching carrier glasses 25 and the frame vine portions 26 does not need to be always transparent, but preferably transparent to expand a field of view at hand of the precise worker, and for example, transparent glass and transparent synthetic resins can be used. In addition, the binocular loupe 2 as shown in FIG. 2 has a magnification of 3.3 to 4.8 times.

Figure 3:
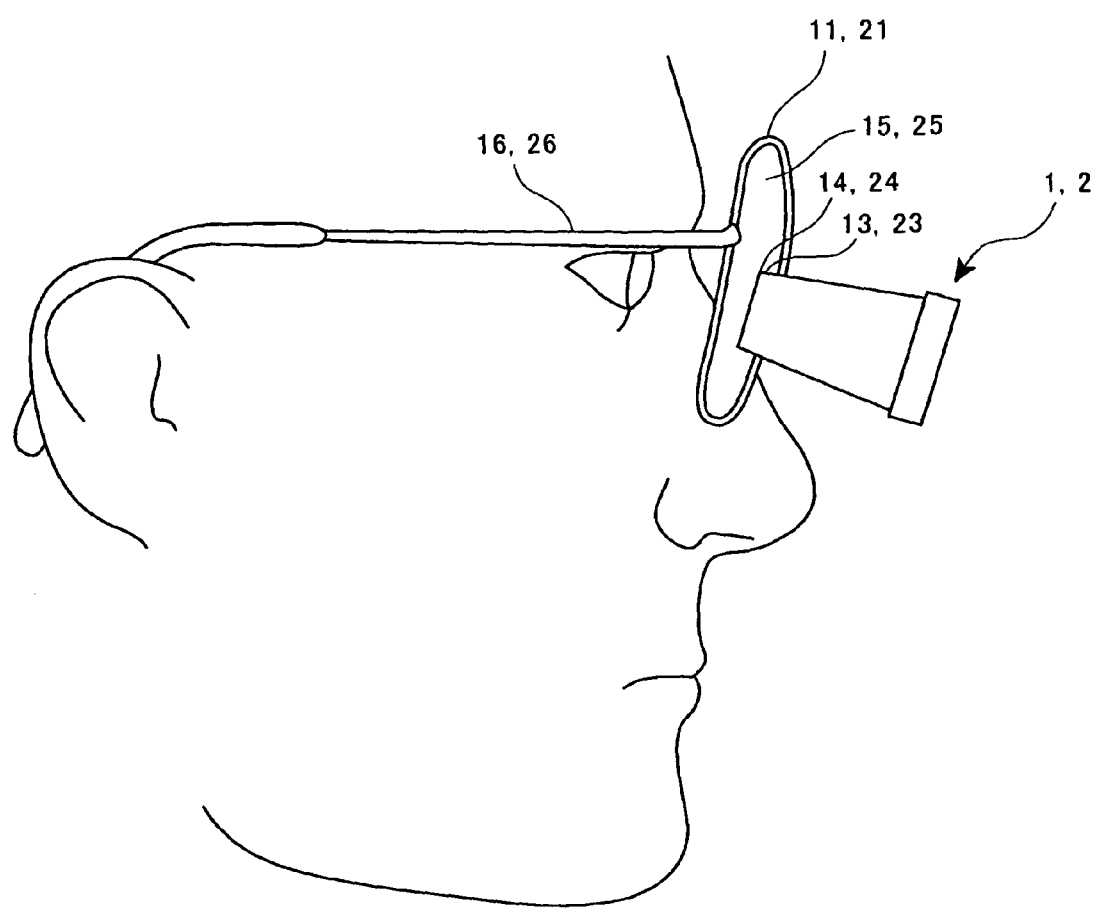
FIG. 3 illustrates a usage pattern of the binocular loupe according to embodiments of the invention.

FIG. 3 is an explanatory diagram illustrating a usage pattern of the binocular loupe according to embodiments of the invention. As shown in FIG. 3, the binocular loupes 1 and 2 according to the embodiments of the invention can be mounted on a face of a precise worker by hanging the frame vine portions 16 and 26 of the glass frames 11 and 21 over ear lobes of the precise worker, respectively.

Figure 4:
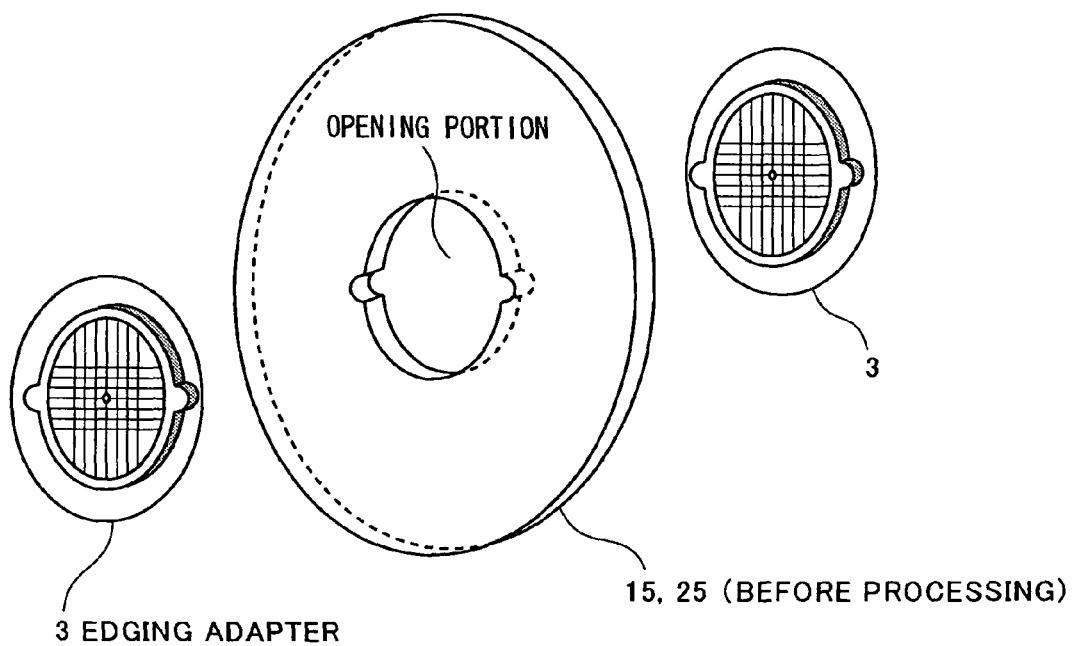
FIGS. 4(a) and 4(b) illustrate a structure of a main-glass attaching carrier lens of the binocular loupe and a structure of a binocular loupe body according to the embodiments of the invention (1/2)
Figure 4:
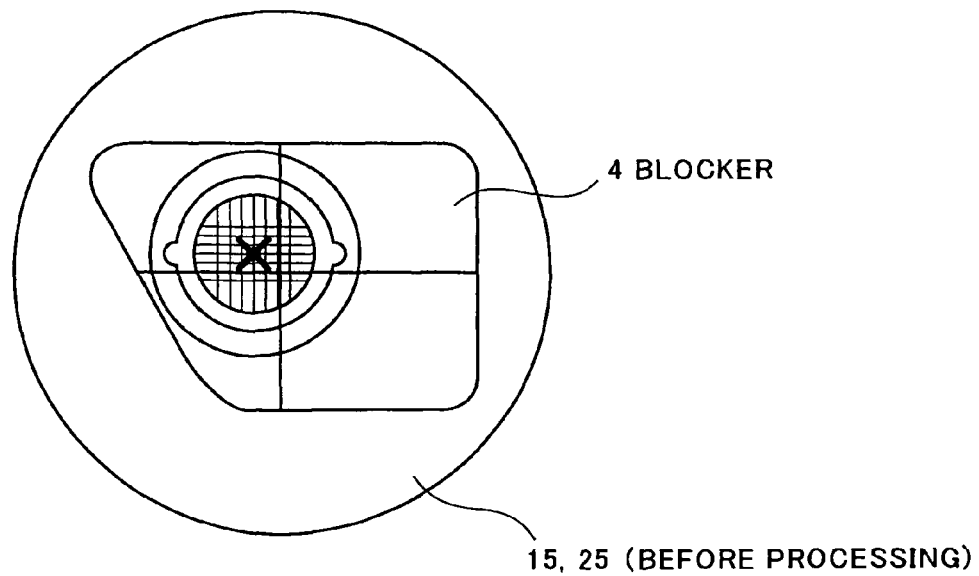

FIGS. 4 and 5 are explanatory diagrams illustrating a processing method of the main-glass attaching carrier lenses of the binocular loupe and an attaching method of the binocular loupe bodies according to the embodiments of the invention. An opening portion is determined by pupillary distance, focal length and angle of line of sight. As shown in FIG. 4(a), two edging adapters 3 are fitted into the opening (hole) of each of the main-glass attaching carrier lenses 15 and 25 from both sides. Further, as shown in FIG. 4(b), using a blocker 4, a position of a fit point is copied to the main-glass attaching carrier lenses 15 and 25 before being processed.

Next, as shown in FIG. 5(c), according to the pattern (finished pattern) of the main-glass attaching carrier lenses 15 and 25 with the copied fit point position, an edger is used to form the shape of the main-glass attaching carrier lenses 15 and 25, and then, a grinder is used to chamfer the lenses. Then, as shown in FIG. 5(c), the chamfered main-glass attaching carrier lenses 15 and 25 are fitted into the main-glass attaching frames 11 and 21, and subsequently, main-glass adapters 5 (structural elements of the main-glass attaching portions 13 and 23) are fitted into the openings (holes) of the main-glass attaching carrier lenses, respectively.

Further, as shown in FIG. 5(d), the binocular loupe bodies 12 and 22 are inserted into the main-glass adapters 5, main-glass attaching rings 6 (structural elements of the main-glass attaching portions 13 and 23) are fitted into screw portions at the back of the binocular loupe bodies 12 and 22 with the main-glass adapters 5 inserted therein, the main-glass attaching rings 6 are screwed, and the binocular loupe bodies 12 and 22 are thereby attached to the main-glass attaching carrier lenses 15 and 25, respectively. In addition, the binocular loupe bodies 12 and 22 may be fixed to the main-glass attaching carrier lenses using an adhesive.

Figure 6:
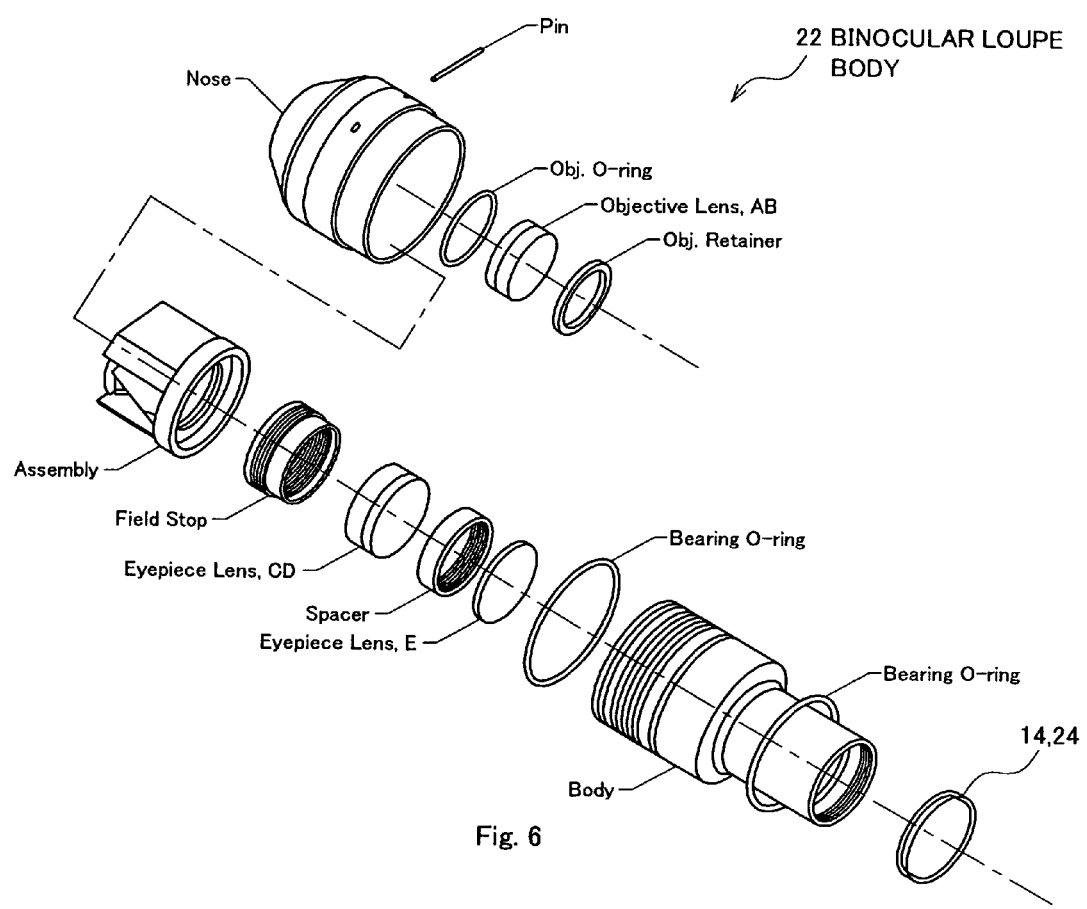
FIG. 6 shows a detailed structure of each of the binocular loupe bodies of the binocular loupe according to the embodiments of the invention.

FIG. 6 is an explanatory view showing a detail structure of each of the binocular loupe bodies of the binocular loupe according to the embodiments of the invention. The focus adjusting portions 14 and 24 are respectively attached detachably to end sides of the binocular loupe bodies 12 and 22 with ease by insertion type or using magnetic absorption.

FIG. 6 shows as an example a detail structure of the optical system of each of the binocular loupe bodies 22 with a magnification of 3.3 times to 4.8 times as shown in FIG. 2, and a detail structure of each of the binocular loupe bodies 12 with a magnification of 2.5 times is almost the same as that as shown in FIG. 6. In addition, as the binocular loupe bodies 12 and 22 according to the invention, commercially available conventional products can be used by being slightly processed.

Figure 7:
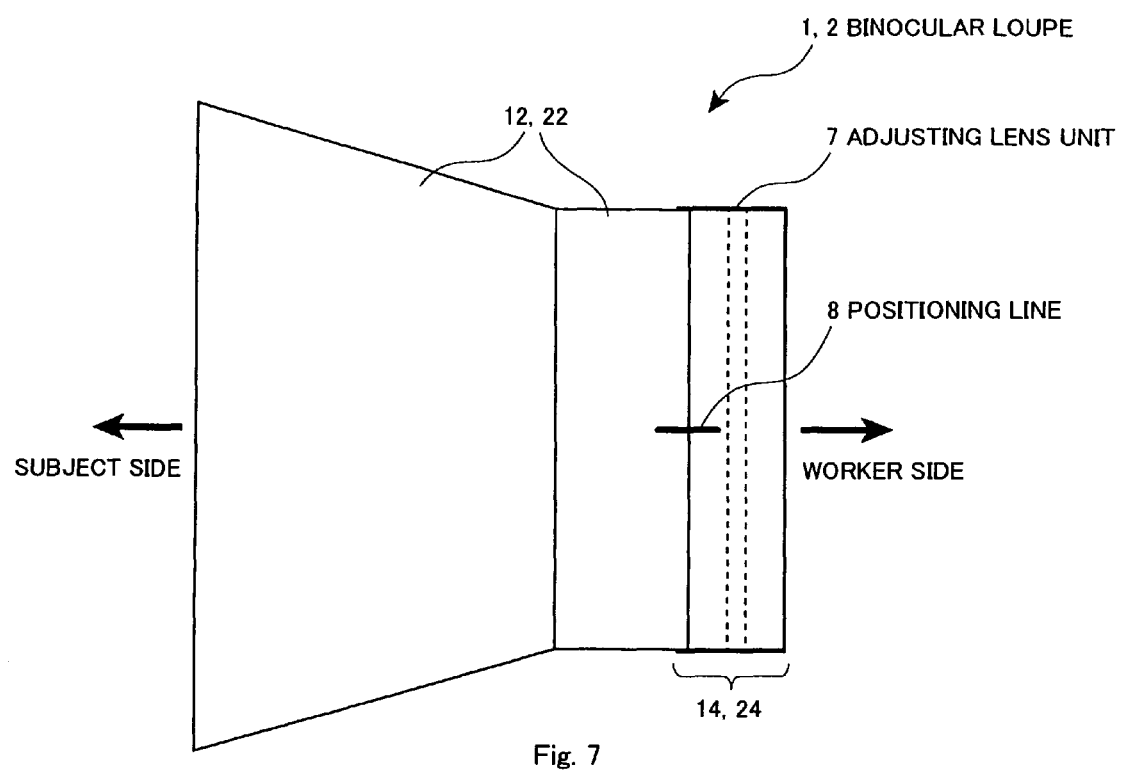
FIG. 7 shows a structure of the binocular loupe according to the embodiments of the invention.

FIG. 7 is a plan view showing a structure of the binocular loupe according to the embodiments of the invention. As described previously, the binocular loupes 1 and 2 according to the embodiments of the invention are comprised of the binocular loupe bodies 12 and 22, and focus adjusting portions 14 and 24 detachable with respect to the binocular loupe bodies 12 and 22, respectively, and each of the focus adjusting portions 14 and 24 is provided with a magnification adjusting lens unit 7 and positioning line 8.

Figure 8:
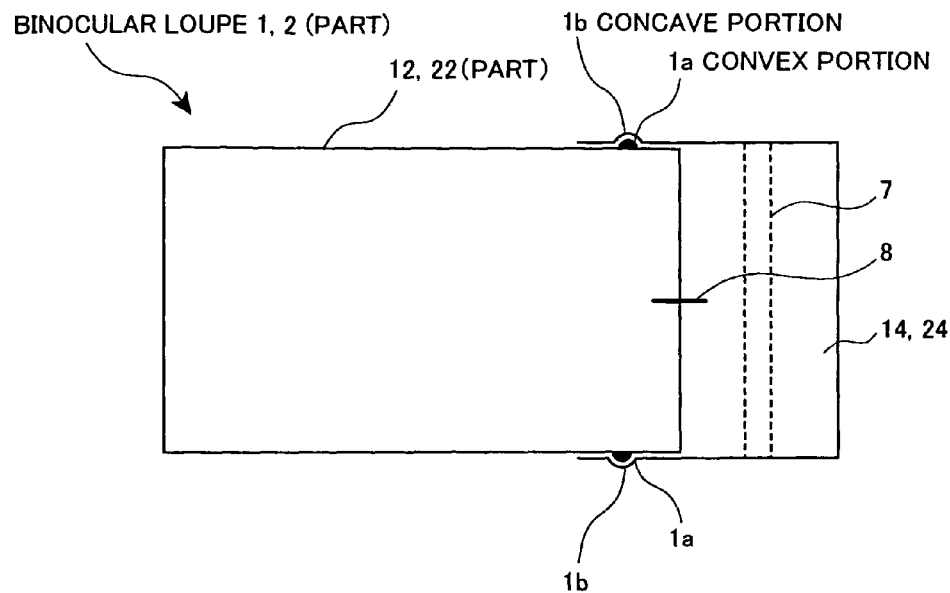
FIGS. 8(a) and 8(b) show a structure of a main-glass attaching portion of focus adjusting means of the binocular loupe according to the embodiments of the invention.
Figure 8:
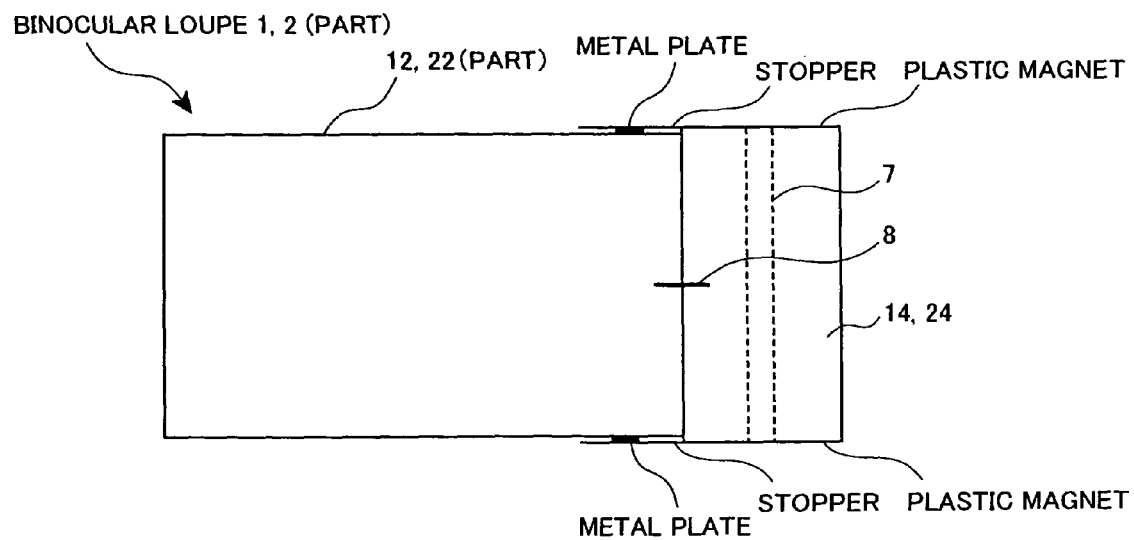

FIG. 8 contains plan views showing a structure of the main-glass attaching portion of the focus adjusting means of the binocular loupe according to the embodiments of the invention. Herein, FIG. 8(a) shows an example of an insertion type, and FIG. 8(b) shows an example of a type of attaching detachably by magnetic force. In the case of the insertion type as shown in FIG. 8(a), in the binocular loupes 1 and 2, the focus adjusting portions 14 and 24 are provided with concave portions 1b, while the binocular loupe bodies 12 and 22 are provided at the back with convex portions 1a, and the convex portions 1b are inserted into the concave portions 1b, whereby the focus adjusting portions 14 and 24 are mounted on the eyepiece portions of the binocular loupe bodies 12 and 22, respectively.

In mounting, by aligning the positioning lines 8 as a single line, it is possible to perform accurate positioning of the focus adjusting portions 14 and 24. By providing positioning lines 8 for positioning, also when directivity exists in the degree of the lens unit 7 to adapt to the case of astigmatism and the like, it is possible to mount the focus adjusting portions 14 and 24 in correct positions. Further, in reverse order of the foregoing, it is possible to remove the focus adjusting portions 14 and 24 from the binocular loupe bodies 12 and 24, respectively.

In addition, the diameter of each of the focus adjusting portions 14 and 24 is set to be slightly larger than a rear outside diameter of each of the binocular loupe bodies 12 and 22, portions of the housings toward the concave portions 1b of the focus adjusting portions 14 and 24 move in the direction of the binocular loupe bodies 12 and 22 while pressing down the convex portions 1a, and that when the positions of the concave portions 1b reach the positions of the convex portions 1a, the convex portions 1a are firmly inserted into the concave portions 1b, respectively (the supporting means=1a+1b).

In the case of the magnetic type as shown in FIG. 8(b), ferromagnetic metal plates are provided on the binocular loupes 1,2 sides, metal magnets or plastic magnets (plastic containing metal powder charged with magnetism) are provided on the focus adjusting portions 14, 24 sides, the plates and magnets are positioned by stoppers and pull each other by magnetic force, and the focus adjusting portions 14 and 24 are thereby attached detachably to the binocular loupes 1 and 2, respectively. The other structure and descriptions thereof are the same as those of the insertion type as shown in FIG. 8(a).

Figure 9:
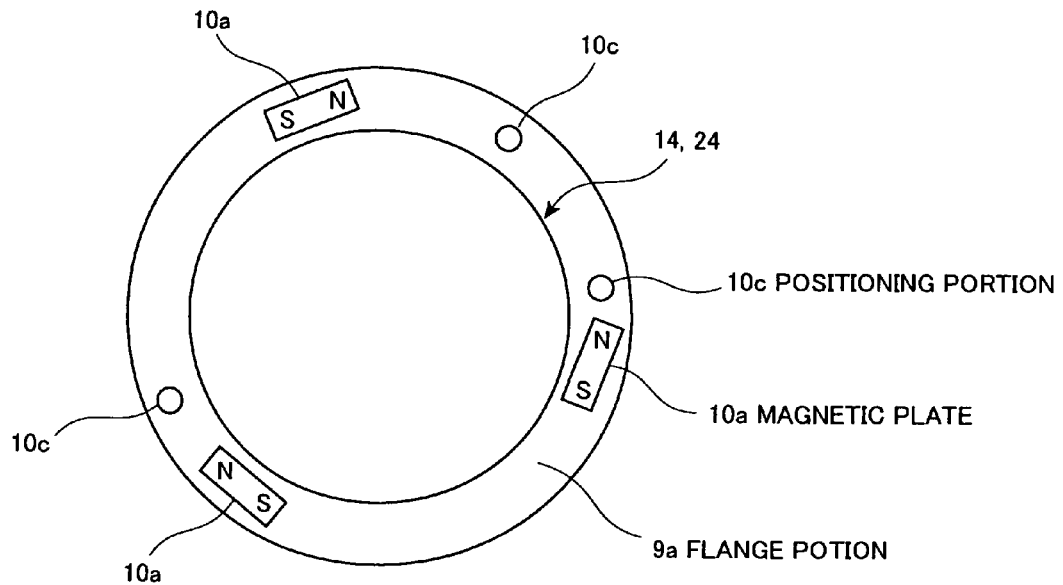
FIGS. 9(a) and 9(b) show another structure of the main-glass attaching portion of the focus adjusting means of the binocular loupe according to the embodiments of the invention.
Figure 9:
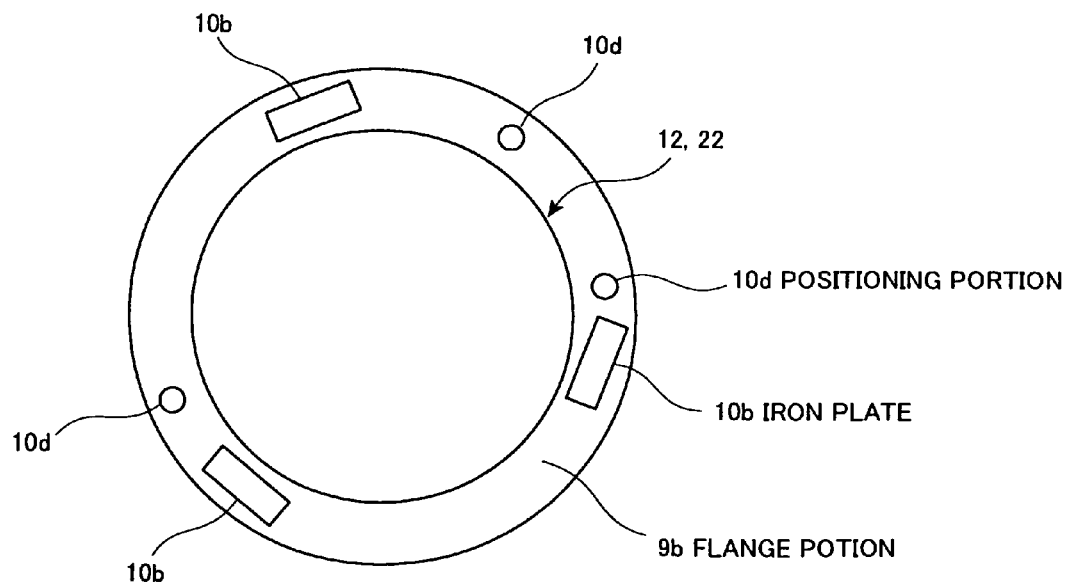

FIG. 9 contains plan views showing another structure of the main-glass attaching portion of the focus adjusting means of the binocular loupe according to the embodiments of the invention. A flange portion 9a is provided at the tip end of each of the focus adjusting portions 14 and 24 as shown in FIG. 9(a), and a plurality of magnetic plates 10a for mounting is embedded or bonded in/to the flange portion 9a. Further, a plurality of positioning portions 10c (convex portions or concave portions) is provided for positioning.

Meanwhile, a flange portion 9b is provided at the rearmost portion (eyepiece portion) of each of the binocular loupe bodies 12 and 22 as shown in FIG. 9(c), and a plurality of iron plates 10b is embedded or bonded in/to the flange portion 9b in positions corresponding to the plurality of magnetic plates 10a. Further, a plurality of positioning portions 10d (convex portions or concave portions) is provided in positions corresponding to the plurality of positioning portions 10c. In addition, it is possible to provide a configuration where the structure of the tip end of each of the focus adjusting portions 14 and 24 and the structure of the rearmost portion of each of the binocular loupe bodies 12 and 22 are exchanged with each other.

Figure 10:
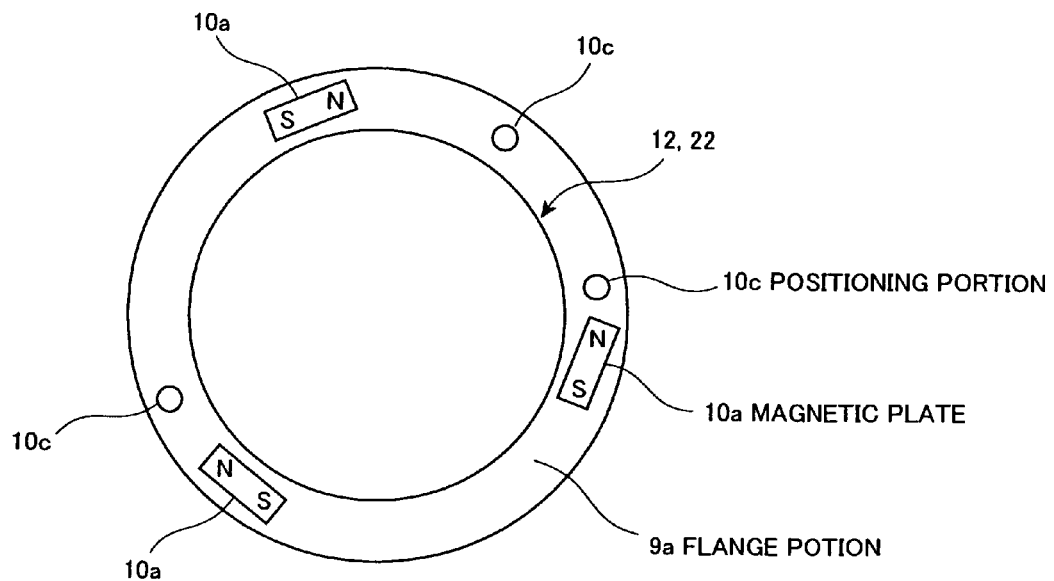
FIGS. 10(a) and 10(b) show another structure of the main-glass attaching portion of the focus adjusting means of the binocular loupe according to the embodiments of the invention.
Figure 10:
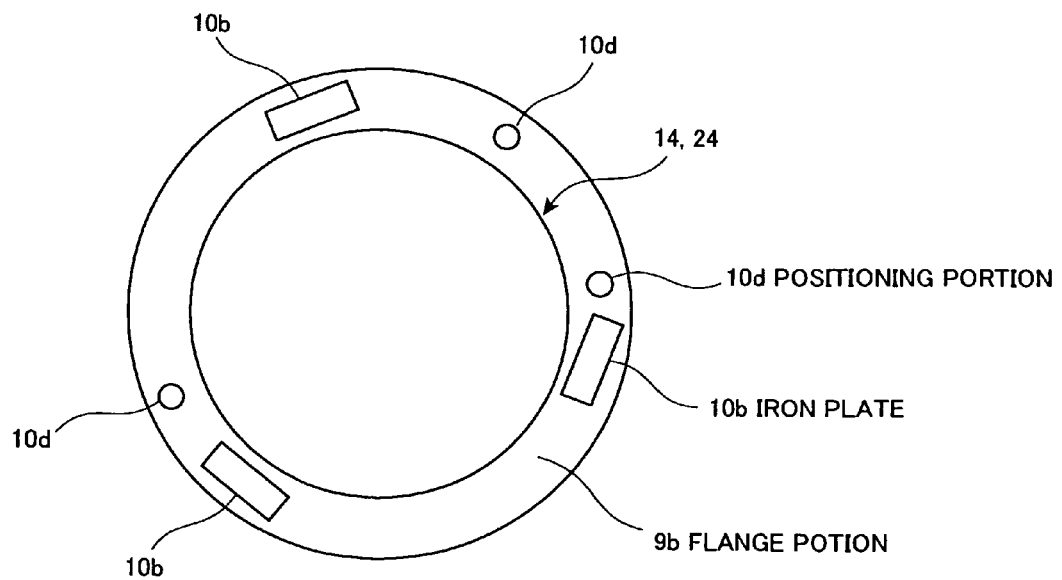

FIG. 10 contains plan views showing another structure of the main-glass attaching portion of the focus adjusting means of the binocular loupe according to the embodiments of the invention. A flange portion 9a is provided at the rearmost portion (eyepiece portion) of each of the binocular loupe bodies 12 and 22 as shown in FIG. 10(a), and a plurality of magnetic plates 10a is embedded or bonded in/to the flange portion 9a. Further, a plurality of positioning portions 10c (convex portions or concave portions) is provided for positioning.

Meanwhile, a flange portion 9b is provided at the tip end of each of the focus adjusting portions 14 and 24 as shown in FIG. 10(b), and a plurality of iron plates 10b is embedded or bonded in/to the flange portion 9a in positions corresponding to the plurality of magnetic plates 10a. Further, a plurality of positioning portions 10d (convex portions or concave portions) is provided in positions corresponding to the plurality of positioning portions 10c.

INDUSTRIAL APPLICABILITY

The present invention relates to s a binocular loupe that is used in medical operations and precise operation and that is capable of supporting varying vision of the user as appropriate.

The invention claimed is:
1. A binocular loupe to magnify a subject at hand to see, comprising:

frame means;

a pair of binocular loupe bodies;

attaching means for fixing the binocular loupe bodies to the frame means;

focus adjusting means for adjusting a focal length of each of the binocular loupe bodies;

supporting means for detachably attaching the focus adjusting means to eyepiece portions of the binocular loupe bodies; and two joint faces having either a magnet plate or an ion plate for joining the focus adjusting means and each of the binocular loupe bodies, wherein the focus adjusting means has magnification adjusting lenses selected from a plurality of different focal lengths which is beforehand prepared, and the focus adjusting means is attached to the supporting means, and wherein each of the two joint faces has a flange portion to enlarge an area of each of the faces, and each of the magnet plate and the ion plate is installed in the flange portion.

2. The binocular loupe according to claim 1, wherein the attaching means comprises a main-glass attaching frame, a main-glass attaching carrier lens which has an opening and is fixed by the main-glass attaching frame, and a main-glass attaching portion fitted into the opening of the main-glass attaching carrier lens.

3. The binocular loupe according to claim 1, wherein each of the focus adjusting means and each of the binocular loupe bodies is provided with either a convex portion or a concave portion to engage the adjusting means and the bodies with one another.

4. The binocular loupe according to claim 3, wherein positioning lines are marked on the focus adjusting means and the binocular loupe bodies to engage the adjusting means and the bodies with one another in predetermined positions.

* * * * *